United States Patent [19]

Bauer et al.

[11] Patent Number: 5,520,724
[45] Date of Patent: May 28, 1996

[54] PROCESS FOR THE RECOVERY OF LOW MOLECULAR WEIGHT $C_{2+}$ HYDROCARBONS FROM A CRACKING GAS

[75] Inventors: Heinz Bauer, Ebenhausen; Hans Becker, München, both of Germany

[73] Assignee: Linde Aktiengesellschaft, Wiesbaden, Germany

[21] Appl. No.: 343,487

[22] PCT Filed: May 12, 1993

[86] PCT No.: PCT/EP93/01180

§ 371 Date: Feb. 3, 1995

§ 102(e) Date: Feb. 3, 1995

[87] PCT Pub. No.: WO93/24428

PCT Pub. Date: Dec. 9, 1993

[30] Foreign Application Priority Data

May 27, 1992 [DE] Germany ............... 42 17 611.5

[51] Int. Cl.⁶ ............... B01D 53/14; B01D 19/00
[52] U.S. Cl. ............... 95/169; 95/180; 95/184; 95/186; 95/193; 95/209; 95/240
[58] Field of Search ............... 95/159, 163–167, 95/169, 179, 180, 184, 186, 193, 209, 227–229, 237–240

[56] References Cited

U.S. PATENT DOCUMENTS

| | | | |
|---|---|---|---|
| 2,529,312 | 11/1950 | Rupp | 95/184 |
| 2,542,520 | 2/1951 | Hibshman | 95/166 |
| 2,573,341 | 10/1951 | Kniel | 95/184 X |
| 2,582,443 | 1/1952 | Linn | 95/237 |
| 2,745,889 | 5/1956 | Johnston et al. | 95/229 X |
| 2,780,580 | 2/1957 | Kniel | 95/184 X |
| 2,804,488 | 8/1957 | Cobb, Jr. | 95/166 X |
| 2,804,939 | 9/1957 | Mattix | 95/184 |
| 2,813,920 | 11/1957 | Cobb, Jr. | 95/179 X |
| 2,815,650 | 12/1957 | McIntire et al. | 95/240 X |
| 2,815,827 | 12/1957 | Jezl et al. | 95/186 |
| 3,034,272 | 5/1962 | Griffin et al. | 95/169 |
| 3,134,726 | 5/1964 | Hochgraf | 95/180 |
| 3,192,732 | 7/1965 | Cahn | 95/180 X |
| 3,557,529 | 1/1971 | Ranke | 95/179 X |
| 3,557,530 | 1/1971 | Voigt et al. | 95/164 |
| 3,695,002 | 10/1972 | Rottmayr et al. | 95/167 |
| 3,816,976 | 6/1974 | Stork et al. | 95/167 X |
| 4,035,167 | 7/1977 | Starks | 55/57 |
| 4,072,604 | 2/1978 | Ward | 95/186 X |
| 4,664,687 | 5/1987 | Bauer | 62/29 |
| 4,747,858 | 5/1988 | Gottier | 95/180 X |
| 5,019,143 | 5/1991 | Mehrta | 95/184 X |

FOREIGN PATENT DOCUMENTS 0185202  1/1990  European Pat. Off. .

*Primary Examiner*—Robert Spitzer
*Attorney, Agent, or Firm*—Millen, White, Zelano, & Branigan

[57] ABSTRACT

The invention relates to a process for the recovery of low molecular weight $C_{2+}$ hydrocarbons, in particular ethylene and ethane from a cracking gas, in particular from a fluid catalytic cracking waste gas. In accordance with the invention the light $C_{2+}$ hydrocarbons are scrubbed out of the cracking gas by absorption, using an organic, preferably paraffinic, physically acting scrubbing agent, the scrubbing agent having a molecular weight of between 50 and 75 g/mol, preferably between 60 and 75 g/mol. Particularly suitable as scrubbing agents are pentane, isopentane or mixtures thereof. Prior to the generation of the loaded scrubbing agent, co-extracted methane is advantageously stripped off.

22 Claims, 1 Drawing Sheet

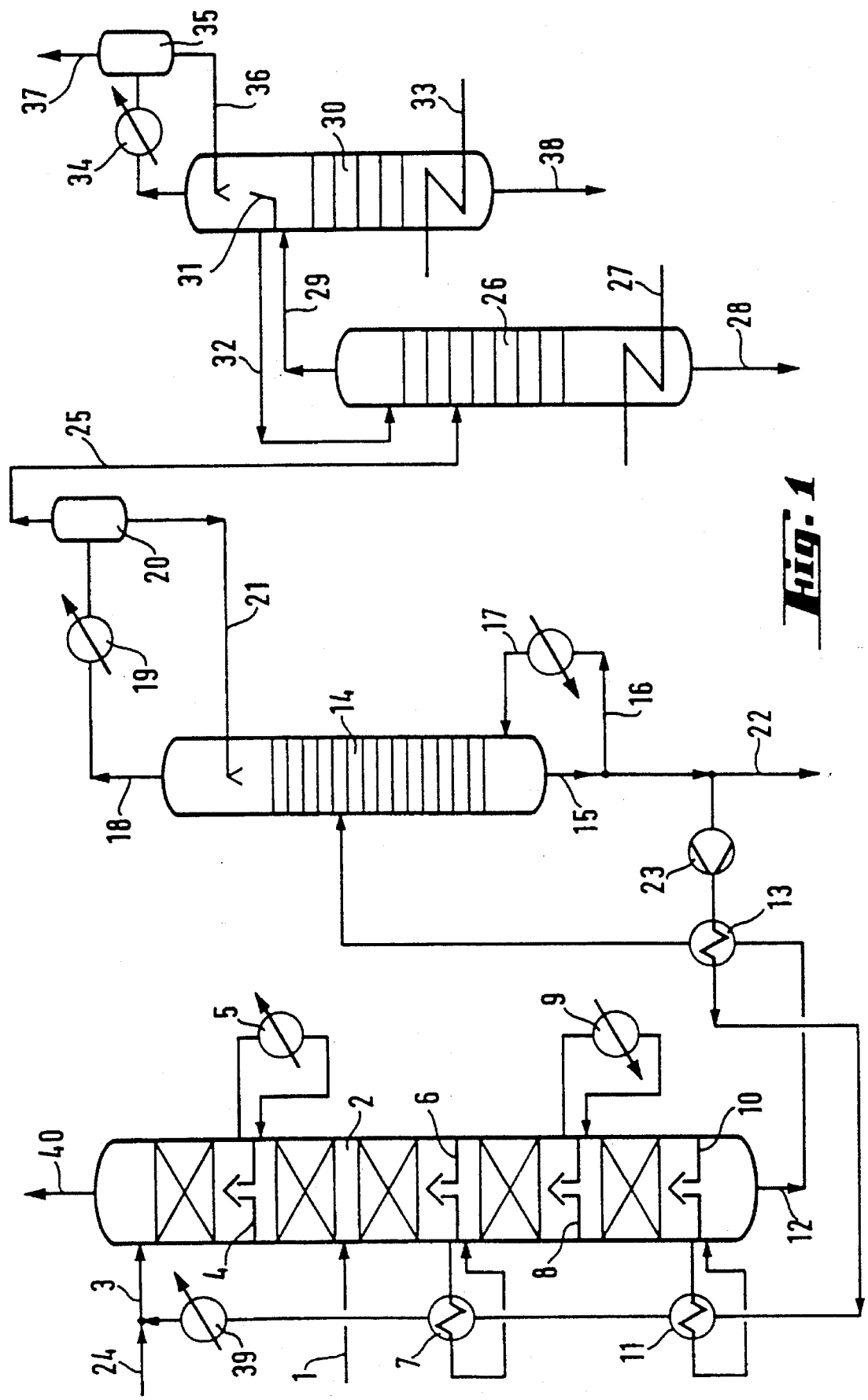

PROCESS FOR THE RECOVERY OF LOW MOLECULAR WEIGHT $C_{2+}$ HYDROCARBONS FROM A CRACKING GAS

The invention relates to a process for the recovery of low molecular weight $C_{2+}$ hydrocarbons, in particular ethylene and ethane, from a gas mixture obtained by the cracking of hydrocarbons and having been freed of high molecular weight hydrocarbons.

In various cracking gas processes, in particular in fluidized catalytic cracking (FCC) a gas mixture is obtained which comprises, inter alia, low molecular weight hydrocarbons, in particular ethylene and ethane, but also $C_3$ and $C_4$ hydrocarbons. In most refineries the high molecular weight hydrocarbons ($C_{5+}$ hydrocarbons) are first separated from the FCC waste gas by fractional distillation. Thereafter, the $C_{3+}$ hydrocarbons are recovered by oil scrubbing, whereas the entire $C_2$ hydrocarbons, but also a certain proportion of $C_{3-}$ and $C_4$ hydrocarbons are discharged into the fuel gas grid.

In the event that $C_2$ hydrocarbons as well are to be recovered from the FCC waste gas, this is done by partial condensation in a low temperature process. Such a process is known for example from EP-B 0 185 202. Because the FCC waste gases invariably contain traces of higher, polyunsaturated hydrocarbons, nitrogen oxides and oxygen, this process always involves a risk that explosive resins may form in the very low temperature items of equipment. A plant with partial condensation in a low temperature process accordingly always entails a certain safety risk. Thus, for example in February, 1990, such a plant exploded in France after having been in operation for eight years. Accordingly, it is an object of the present invention to provide a process of the type as set out in the introduction, wherein the $C_{2+}$ hydrocarbons can be recovered from the input gas in a simple manner, but where the safety of the plant is warranted by a special mode of operation.

This object is attained according to the invention in that the low molecular weight $C_{2+}$ hydrocarbons are scrubbed from the gas mixture by absorption by means of an organic, preferably paraffinic, physically acting scrubbing agent in an absorption column, the scrubbing agent having a molecular weight between 50 and 75 g/mol, preferably between 60 and 75 g/mol, the scrubbing agent being passed in a circuit to be first loaded with low molecular weight hydrocarbons, being regenerated in a regenerating column and subsequently being returned into the absorption column for renewed loading.

The process according to the invention offers the advantage that the low molecular weight hydrocarbons are removed from the gas mixture during gas scrubbing, thereby avoiding a safety risk in that the formation of explosive resins is prevented by this procedure.

Advantageously, a $C_{4+}$ hydrocarbon fraction, preferably pentane, isopentane or mixtures thereof, is employed as a scrubbing agent. Such a scrubbing agent is characterized by a very high solvent power for $C_2$ hydrocarbons, in particular ethylene and ethane, but also for other readily soluble components. Light gasoline comprising proportions within the above described molecular weight range, in particular pentane compounds are obtained during the pretreatment of the feed gas, for example in the fractional distillation, and are accordingly readily available.

In a preferred embodiment of the process according to the invention the loaded scrubbing agent, prior to its being fed into the regeneration column, is stripped with a stripping gas, resulting in particular in the stripping off of co-absorbed methane. The methane thereby recovered can be further processed or may, for example, be used as a fuel gas.

Particular advantages result if the stripping of the loaded scrubbing agent is conducted in a lower section of the absorption column. This procedure, apart from simplifications in respect of apparatus requirements, offers the advantage that methane dissolved in the scrubbing agent can even be stripped off from the scrubbing agent in the absorption region in addition to the stripping region, since the stripping gas can flow through the entire absorption column.

Further advantages result from using evaporated scrubbing agent as a stripping gas. For this purpose, heat is introduced into the lower region of the absorption column, for example by a boiling vessel, causing a certain part of the scrubbing agent to evaporate. Due to the lower temperatures in the upper region of the absorption column, the evaporated scrubbing agent is condensed once again and can be reloaded with low molecular weight hydrocarbons. Stripping with a foreign stripping gas might result in contamination of the ethylene product flow.

The gas mixture is advantageously fed into the absorption column at a pressure of 4 to 50 bar, preferably 10 to 30 bar. Although an elevated pressure during absorption entails increased energy expenditures, it also substantially decreases the amount of required scrubbing agent. Thus, for example, the scrubbing agent throughput required may be reduced by half if the pressure is increased from 4 bar to 30 bar.

Advantageously, the absorption is carried out at temperatures between 0° and −50° C., preferably between −30° and −50° C., particularly preferably between −35° and −45° C. Although even lower temperatures increase the solvent power of the scrubbing agent for the low molecular weight hydrocarbons, they, on the other hand, may cause a possible increase of $NO_2$ formation. Therefore, when employing feed flows having a relatively high $NO_x$ content, a comparatively high temperature for the absorption should be selected. The cold overhead product of the absorption column can be employed for cooling the cracking gas mixture.

After the components lighter than ethylene, for example methane, have been stripped off the loaded scrubbing agent, the scrubbing agent loaded with $C_{2+}$ hydrocarbons is passed into a regenerating column. The regenerating column is operated at temperatures higher than during the absorption. The highest temperatures in the process according to the invention prevail in the lower region of the regenerating column. There the scrubbing agent is heated preferably by means of a boiling vessel in order to obtain desorption of the $C_{3-}$ hydrocarbons from the scrubbing agent. The temperatures in the sump of the regenerating column are thus advantageously so selected that 120° C., preferably 105° C. is not exceeded. The reason is that it was found that polymerization for example to form butadiene will then be avoided. It is difficult to remove polymerization products from the scrubbing agent. Accordingly, the temperature in the sump region of the regenerating column is predetermined at the lower limit by an inadequate desorption of the $C_{3-}$ hydrocarbons from the scrubbing agent and at the upper limit by incipient polymerization.

In principle, it is possible for the regeneration of the scrubbing agent to be performed at a pressure which is lower or higher than that for the absorption. However, preferably the pressure in the regenerating column is below that of the absorption column.

From the head of the regenerating column a gas flow is withdrawn, partly condensed, passed into a separator and the condensate reintroduced from the separator as reflux into the regenerating column for reducing the losses of scrubbing agent. In addition, a product gas flow rich in $C_2/C_3$ hydrocarbons is recovered by the separator. $C_{4+}$ hydrocarbons passed into the regeneration are returned from the sump of the regenerating column to the absorption column jointly with or serving as regenerated scrubbing agent.

In accordance with a further development of the process according to the invention, the head product of the regenerating column is partly condensed and after the condensate has been separated and returned into the regenerating column, the $C_2$ and $C_3$ hydrocarbon-rich gas flow is subjected to a $C_2/C_3$ separation. In the $C_2/C_3$ separation a $C_2$ hydrocarbon flow is recovered which in a further separating stage is separated into ethylene- and ethane-containing product gas flow.

In the following the invention will be further elucidated with reference to a working example.

BRIEF DESCRIPTION OF THE DRAWING

FIG. 1 illustrates a process according to the invention including absorption, regeneration and further separation of the $C_2$ and $C_3$ hydrocarbons by distillation.

It is to be noted that the totals of the data listed in the individual tables concerning the composition of individual flows, due to approximations may exceed 100%.

By way of duct 1 an FCC cracking waste gas, freed by fractional distillation of $C_{4+}$ hydrocarbons and dried, is fed into the absorption column 2 at a pressure of 13.3 bar and a temperature of 22° C. In this case the FCC waste gas has the following composition:

| | |
|---|---|
| $H_2$ | 3.4 Weight % |
| $N_2$ | 11.8 Weight % |
| CO | 1.1 Weight % |
| $CH_4$ | 31.6 Weight % |
| $C_2H_4$ | 20.5 Weight % |
| $C_2H_6$ | 28.4 Weight % |
| $C_3H_6$ | 2.0 Weight % |
| $C_3H_8$ | 1.0 Weight % |
| other components | <0.1 Weight % |

By way of duct 3 regenerated scrubbing agent composed to about three quarters of pentane and to about one quarter of isopentane is fed into the upper region of the absorption column 2 at a temperature of −40° C. and a pressure of 13.1 bar. Above the chimney tray 4 the scrubbing agent is withdrawn, cooled in the side cooler 5 in order to withdraw the process heat formed and once again introduced into the absorption column. Above the chimney tray 6 loaded scrubbing agent is warmed up by indirect heat exchange (7) with regenerated scrubbing agent and returned again into the absorption column 2. Above the chimney tray 8 the scrubbing agent is once again withdrawn and further heated in the boiler vessel 9, before once again being fed into the absorption column 2 underneath the chimney tray 8. Above the chimney tray 10 the scrubbing agent is once again withdrawn and further heated by indirect heat exchange (11) with regenerated scrubbing agent and is fed into the lowermost section of the absorption column 2. The three column sections below the inlet of feed duct 1 serve for the removal of components lighter than ethylene from the scrubbing agent. By the heating of the scrubbing agent, scrubbing agent vapor is formed which is employed as stripping gas for stripping off the components which are lighter than ethylene, in particular methane. Overhead of the absorption column 2 a gas flow is thus withdrawn which is virtually free of $C_{2+}$ hydrocarbons and which has the following composition:

| | |
|---|---|
| $H_2$ | 6.7 Weight % |
| $N_2$ | 23.0 Weight % |
| $O_2$ | 0.1 Weight % |
| CO | 2.2 Weight % |
| $CH_4$ | 61.6 Weight % |
| and traces of $C_{2+}$ hydrocarbons. | |

From the sump of the absorption column 2 a scrubbing agent loaded with $C_{2+}$ hydrocarbons and having a temperature of 54° C. and a pressure of 13.4 bar is withdrawn:

| | |
|---|---|
| $C_2H_4$ | 3.4 Weight % |
| $C_2H_6$ | 5.2 Weight % |
| $C_3H_6$ | 0.8 Weight % |
| $C_3H_8$ | 0.3 Weight % |
| $C_5H_{12}$ | 65.6 Weight % |
| $C_5H_{12}$ (Iso) | 24.6 Weight % |
| other components | <0.1 Weight % |

The loaded scrubbing agent from duct 12 is further heated by indirect heat exchange (13) with indirect scrubbing agent and introduced into the regenerating column 14. In the regenerating column 14 the hot regeneration of the scrubbing agent takes place. For this purpose, regenerated scrubbing agent from the sump of the regenerating column (15) is partly (16) heated in the boiling vessel 17 to 105° C. and returned into the lower region of the regenerating column. The scrubbing agent vapor thereby formed strips the $C_2$ and $C_3$ hydrocarbons from the scrubbing agent. The overhead product of the regenerating column (18) having a temperature of 57° C. and a pressure of 7.6 bar is cooled in a condenser 19 and introduced into a separator 20. Components which have condensed out, for the predominant part scrubbing agent which has condensed out, are returned from the separator 20 via line 21 into the upper region of the regenerating column 14. The scrubbing agent flow withdrawn from the sump of the regenerating column 14 by way of duct 15 at a temperature of 102° C. and a pressure of 7.8 bar and which is not returned by way of duct 16 into the regenerating column is raised by pump 23 to a pressure of 14 bar and cooled in the heat exchangers 13, 11, 7 and 39 to −40° C. The composition of the regenerated scrubbing agent withdrawn from the regenerating column is as follows:

| | |
|---|---|
| $C_2H_6$ | 0.4 Weight % |
| $C_3H_6$ | 0.5 Weight % |
| $C_3H_8$ | 0.2 Weight % |
| $C_5H_{12}$ | 72.0 Weight % |
| $C_5H_{12}$ (Iso) | 27.0 Weight % |
| other components | <0.1 Weight % |

By way of duct 22 a small amount of scrubbing agent purge is separated off. A corresponding amount of scrubbing agent is added to the cooled scrubbing agent in duct 3 by way of duct 24.

By the separator 20 a $C_2$-/$C_3$ hydrocarbon gas mixture is recovered in the duct 25 having the following composition:

| | |
|---|---|
| $C_2H_4$ | 38.7 Weight % |
| $C_2H_6$ | 55.2 Weight % |
| $C_3H_6$ | 3.7 Weight % |
| $C_3H_8$ | 1.9 Weight % |
| $C_5H_{12}$ | 0.2 Weight % |
| $C_5H_{12}$ (Iso) | 0.4 Weight % |
| other | <0.1 Weight % |

This gas flow is subsequently passed to a fractional distillation and for this purpose is first introduced into column 26 for a C$_2$-/C$_3$ hydrocarbon separation. Column 26 is equipped with sump heating 27. From the sump of the column 26 a distillate (LPG) which is essentially composed of C$_3$ hydrocarbons is withdrawn by way of duct 28, with the following composition:

| | |
|---|---|
| C$_3$H$_6$ | 58.8 Weight % |
| C$_3$H$_8$ | 30.9 Weight % |
| C$_4$H$_6$ | 0.3 Weight % |
| C$_5$H$_{12}$ | 3.2 Weight % |
| C$_5$H$_{12}$ (Iso) | 6.7 Weight % |
| other components | <0.1 Weight % |

The overhead product of C$_2$ hydrocarbons having the following composition:

| | |
|---|---|
| C$_2$H$_4$ | 36.9 Weight % |
| C$_2$H$_6$ | 62.9 Weight % |
| C$_3$H$_6$ | 0.1 Weight % |
| other components | <0.1 Weight % | is fed by way of ducts 29 into the column 30. In order to keep the C$_3$H$_6$C$_3$H$_{8+}$ components in duct 29 as low as possible, the flow 32 withdrawn above the side tray 31 is returned as reflux into the upper region of the column 26. The reflux 32 has the following composition:

| | |
|---|---|
| C$_2$H$_4$ | 24.6 Weight % |
| C$_2$H$_6$ | 75.3 Weight % |
| other components | <0.1 Weight % |

Column 30 serves for splitting the C$_2$ compounds. For this purpose, the sump region of column 30 is heated by way of the sump heating means 33 while the overhead product is partly condensed (34), and the condensate withdrawn by a separator 35 is returned as reflux into the column 30 by way of duct 36, there to attain a back-washing of the components which are heavier than ethylene. More than 99.9% of the overhead product of column 30 is represented by ethylene, so that by way of duct 37 a pure ethylene product flow with minimal contaminations is recovered. A sump product having the composition:

| | |
|---|---|
| C$_2$H$_4$ | 0.9 Weight % |
| C$_2$H$_6$ | 98.8 Weight % |
| C$_3$H$_6$ | 0.3 Weight % |
| other components | <0.1 Weight % | is withdrawn by way of duct 38 from the sump of the column 30. This ethane fraction from duct 38 may for example be mixed with the overhead product of the absorption column 2 in duct 40 and be used as a fuel gas.

The columns 26 and 30 may be combined in a single column in which case from the head of this column likewise an ethylene flow is recovered, whereas from the sump of the column a C$_3$ hydrocarbon/ethane mixture is withdrawn.

We claim:

1. A process for recovery of low molecular weight C$_{2+}$ hydrocarbons, comprising ethylene and ethane, from a gas mixture obtained by the cracking of hydrocarbons and having been freed of high molecular weight hydrocarbons, said process comprising:

scrubbing low molecular weight C$_{2+}$ hydrocarbons from said gas mixture by absorption with an organic physically acting scrubbing agent in an absorption column, said scrubbing agent having a molecular weight between 50 and 75 g/mol, wherein said scrubbing agent is passed in a circuit whereby the scrubbing agent is first loaded with low molecular weight hydrocarbons, then regenerated in a regenerating column and subsequently returned into said absorption column for renewed loading, wherein the loaded scrubbing agent, prior to being fed into said regenerating column, is stripped with a stripping gas, whereby co-absorbed methane is stripped off.

2. A process according to claim 1, wherein a C$_{4+}$ hydrocarbon fraction is employed as the scrubbing agent.

3. A process according to claim 2, wherein the scrubbing agent is pentane, isopentane, or mixtures thereof.

4. A process according to claim 1, wherein stripping of said loaded scrubbing agent is carried out in a lower section of said absorption column.

5. A process according to claim 4, wherein evaporated scrubbing agent is employed as said stripping gas.

6. A process according to claim 1, wherein evaporated scrubbing agent is employed as said stripping gas.

7. A process according to claim 1, wherein said gas mixture is fed into said absorption column at a pressure of 4 to 50 bar.

8. A process according to claim 7, wherein the pressure is 10–30 bar.

9. A process according to claim 1, wherein the absorption is carried out at temperatures between 0° and −50° C.

10. A process according to claim 9, wherein the adsorption temperature is between −30° and −50° C.

11. A process according to claim 9, wherein the adsorption temperature is between −35° and −45° C.

12. A process according to claim 1, wherein the temperature in the sump of said regenerating column does not exceed 120° C.

13. A process according to claim 12, wherein the temperature in the sump does not exceed 105° C.

14. A process according to claim 1, wherein the pressure in said regenerating column is below that of said absorption column.

15. A process according to claim 1, wherein gas containing C$_2$ hydrocarbons and C$_3$ hydrocarbons is withdrawn from the head of said regenerating column, subjected to partial condensation and separated from condensate, and then subjected to a C$_2$/C$_3$ separation, and C$_2$ hydrocarbons are withdrawn from the C$_2$/C$_3$ separation and separated further into ethylene- and ethane-containing product gas flows.

16. A process according to claim 1, wherein the scrubbing agent is paraffinic.

17. A process according to claim 1, wherein the molecular weight of the scrubbing agent is between 60 and 75 g/mol.

18. A process according to claim 1, further comprising withdrawing a gas flow from the head of said regenerating column, subjecting said gas flow to partial condensation, introducing the partially condensed gas flow into a separator wherein said partially condensed gas flow is separated into a condensate and a C$_2$/C$_3$ hydrocarbon product gas flow, and said condensate is reintroduced to said regenerating column as reflux.

19. A process according to claim 18, wherein said $C_2/C_3$ hydrocarbon product gas flow is subjected to fractional distillation from which a $C_3$ hydrocarbon product stream is obtained as a bottom stream and a $C_2$ hydrocarbon product stream is obtained as an overhead stream.

20. A process according to claim 19, wherein said $C_2$ hydrocarbon product stream is delivered to a column for splitting of the $C_2$ hydrocarbons from which an ethylene product stream is obtained as an overhead stream and an ethane product stream is obtained as a bottom stream.

21. A process according to claim 1, wherein said gas mixture is a waste gas from a fluidized catalytic cracking unit and wherein, prior to introduction into said absorption column, $C_{4+}$ hydrocarbons are removed from said waste gas by fractional distillation.

22. A process for the recovery of $C_{2+}$ hydrocarbons from a gas mixture containing ethylene and ethane, said process comprising:

introducing said gas mixture into an absorption/stripper column, wherein a scrubbing agent is introduced into said absorption/stripper column at a point above the introduction of said gas mixture, and said scrubbing agent is removed from said absorber/stripper column at at least one point below the point of introduction of said gas mixture, heated and reintroduced into said absorber/stripper column at a point below the introduction of said gas mixture, whereby the scrubbing agent vapor resulting from the heating of the removed scrubbing agent acts as a stripping gas for stripping off co-absorbed methane from said scrubbing agent;

removing loaded scrubbing agent from the bottom of said absorption/stripper column, heating said loaded scrubbing agent by indirect heat exchange, and introducing the heated, loaded scrubbing agent into a regeneration column;

removing regenerated scrubbing agent from the bottom of said regeneration column and recycling said regenerated scrubbing agent to the top of said absorption/stripper column; and removing a $C_2/C_3$ hydrocarbon gas stream from the head of said regeneration column, cooling said $C_2/C_3$ hydrocarbon gas stream in a condenser and delivering the resultant partially condensed $C_2/C_3$ hydrocarbon stream into a separator from which a condensate stream is removed and reintroduced into the upper region of said regeneration column and a product $C_2/C_3$ hydrocarbon gas mixture containing ethane and ethylene is also removed from said separator.

* * * * *

REEXAMINATION CERTIFICATE (3512th)

United States Patent [19]
Bauer et al.

[11] B1 5,520,724
[45] Certificate Issued May 5, 1998

[54] PROCESS FOR THE RECOVERY OF LOW MOLECULAR WEIGHT $C_{2+}$ HYDROCARBONS FROM A CRACKING GAS

[75] Inventors: Heinz Bauer, Ebenhausen; Hans Becker, München, both of Germany

[73] Assignee: Linde Aktiengesellschaft, Wiesbaden, Germany

Reexamination Request:
No. 90/004,512, Jan. 9, 1997

Reexamination Certificate for:
Patent No.: 5,520,724
Issued: May 28, 1996
Appl. No.: 343,487
Filed: Feb. 3, 1995

[22] PCT Filed: May 12, 1993
[86] PCT No.: PCT/EP93/01180
§ 371 Date: Feb. 3, 1995
§ 102(e) Date: Feb. 3, 1995
[87] PCT Pub. No.: WO93/24428
PCT Pub. Date: Dec. 9, 1993

[30] Foreign Application Priority Data
May 27, 1992 [DE] Germany ............... 42 17 611.5

[51] Int. Cl.$^6$ ............... B01D 53/14; B01D 19/00
[52] U.S. Cl. ............... 95/169; 95/180; 95/184; 95/186; 95/193; 95/209; 95/240
[58] Field of Search ............... 95/159, 163–167, 95/169, 179, 180, 184, 186, 193, 209, 227–229, 237–240; 585/809

[56] References Cited

U.S. PATENT DOCUMENTS

| | | | |
|---|---|---|---|
| 2,765,635 | 10/1956 | Redcay | 62/122 |
| 5,019,143 | 5/1991 | Mehra | 62/17 |
| 5,220,097 | 6/1993 | Lam et al. | 585/809 |

*Primary Examiner*—Robert H. Spitzer

[57] ABSTRACT

The invention relates to a process for the recovery of low molecular weight $C_{2+}$ hydrocarbons, in particular ethylene and ethane from a cracking gas, in particular from a fluid catalytic cracking waste gas. In accordance with the invention the light $C_{2+}$ hydrocarbons are scrubbed out of the cracking gas by absorption, using an organic, preferably paraffinic, physically acting scrubbing agent, the scrubbing agent having a molecular weight of between 50 and 75 g/mol, preferably between 60 and 75 g/mol. Particularly suitable as scrubbing agents are pentane, isopentane or mixtures thereof. Prior to the generation of the loaded scrubbing agent, co-extracted methane is advantageously stripped off.

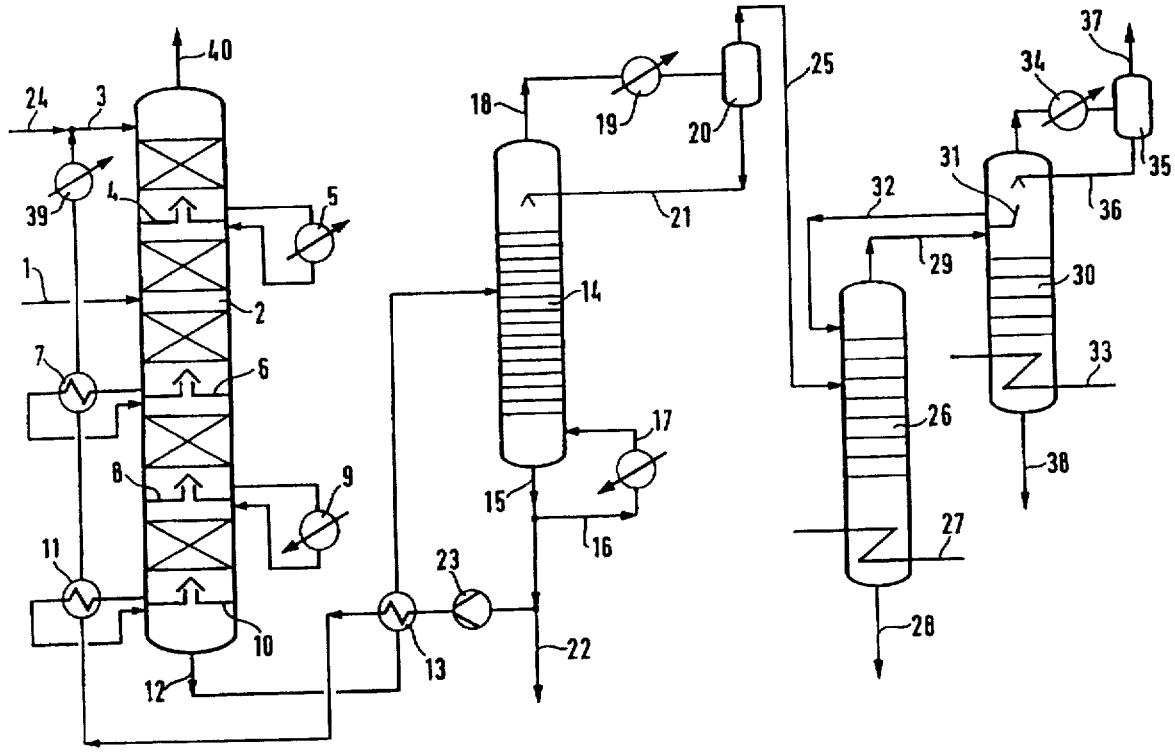

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 4–17 and 20–22 are cancelled.

Claims 3 and 18 are determined to be patentable as amended.

Claim 19 dependent on an amended claim, is determined to be patentable.

New claims 23–27 are added and determimed to be patentable.

3. A process according to [claim 2] *claim 23*, wherein the scrubbing agent is pentane, isopentane, or mixtures thereof.

18. A process according to [claim 1] *claim 23*, further comprising [withdrawing a gas flow] *subjecting said $C_2/C_3$ fraction* from the head of said regenerating column[, subjecting said gas flow] to partial condensation, introducing the partially condensed gas flow into a separator wherein said partially condensed gas flow is separated into a condensate and a $C_2/C_3$ hydrocarbon product gas flow, and said condensate is reintroduced to said regenerating column as reflux.

*23. A process for recovery of low molecular weight $C_{2+}$ hydrocarbons, comprising ethylene and ethane, from a gas mixture containing methane, ethylene, ethane and appreciable amounts of $C_3$ hydrocarbons, said gas mixture obtained by the cracking of hydrocarbons and having been freed of $C_{4+}$ hydrocarbons, said process comprising:*

*scrubbing low molecular weight $C_{2+}$ hydrocarbons from said gas mixture by absorption with an organic physically acting scrubbing agent in an absorption column, wherein all of said scrubbing agent is a $C_{4+}$ hydrocarbon fraction having a molecular weight between 50 and 75 g/mol,*

*passing said scrubbing agent in a circuit whereby the scrubbing agent is first loaded in said absorption column with low molecular weight hydrocarbons and removed as a bottoms stream from said absorption column then regenerated in a regenerating column and subsequently returned into said absorption column for renewed loading wherein the loaded scrubbing agent, prior to being fed into said regenerating column, is stripped with a stripping gas, whereby co-absorbed methane is stripped off, and*

*removing $C_2/C_3$ hydrocarbon fraction as an overhead stream from said regenerating column.*

*24. A process according to claim 23 wherein the regenerated scrubbing agent exhibits a higher weight percent of $C_3$ hydrocarbons than $C_2$ hydrocarbons.*

*25. A process according to claim 23 wherein, said scrubbing agent is paraffinic.*

*26. A process according to claim 23, wherein the molecular weight of said scrubbing agent is between 60 and 75 g/mol.*

*27. A processing according to claim 26, wherein gas containing $C_2$ hydrocarbons and $C_3$ hydrocarbons is withdrawn from the head of said regenerating column, subjected to partial condensation and separated from condensate, and then subjected to a $C_2/C_3$ separation, and*

*$C_2$ hydrocarbons are withdrawn from the $C_2/C_3$ separation and separated further into ethylene-and ethane-containing product gas flows.*

\* \* \* \* \*